(12) United States Patent
Walla et al.

(10) Patent No.: US 7,170,598 B2
(45) Date of Patent: Jan. 30, 2007

(54) MULTI-PARAMETER FLUORIMETRIC ANALYSIS IN A MASSIVELY PARALLEL MULTI-FOCAL ARRANGEMENT AND THE USE THEREOF

(75) Inventors: Peter Jomo Walla, Cologne (DE);
Andre Koltermann, Cologne (DE);
Ulrich Kettling, Cologne (DE);
Mathias Scharte, Cologne (DE)

(73) Assignee: Direvo Biotech AG, Nattermannallee (DE)

( * ) Notice: Subject to any disclaimer, the term of this patent is extended or adjusted under 35 U.S.C. 154(b) by 433 days.

(21) Appl. No.: 10/688,101

(22) Filed: Oct. 17, 2003

(65) Prior Publication Data

US 2004/0125372 A1 Jul. 1, 2004

Related U.S. Application Data

(60) Provisional application No. 60/419,299, filed on Oct. 17, 2002.

(51) Int. Cl.
*G01J 3/30* (2006.01)

(52) U.S. Cl. .................................. 356/318; 250/458.1

(58) Field of Classification Search ................ 356/317, 356/417, 318, 418; 422/82.07–82.08; 250/458.1–461.2; 436/172
See application file for complete search history.

(56) References Cited

U.S. PATENT DOCUMENTS 5,252,834 A   10/1993  Lin

| | | | |
|---|---|---|---|
| 6,229,635 B1 * | 5/2001 | Wulf | ........................... 359/196 |
| 6,262,423 B1 | 7/2001 | Hell et al. | |
| 6,455,861 B1 * | 9/2002 | Hoyt | ....................... 250/458.1 |
| 6,603,537 B1 * | 8/2003 | Dietz et al. | ................... 356/39 |
| 2002/0070349 A1 | 6/2002 | Hoyt | |

FOREIGN PATENT DOCUMENTS

| EP | 0 424 934 A2 | 5/1991 |
|---|---|---|
| WO | WO 00/11024 A2 | 3/2000 |
| WO | WO 02/14838 A2 | 2/2002 |

OTHER PUBLICATIONS

Abstract of Japan, 2002005834, Kenji, "Distribution Measuring Apparatus for Fluorescence Labeled Substance," (Jan. 9, 2002).

* cited by examiner

*Primary Examiner*—Hwa (Andrew) Lee
*Assistant Examiner*—Marissa J. Detschel
(74) *Attorney, Agent, or Firm*—Caesar, Rivise, Bernstein, Cohen & Pokotilow, Ltd.

(57) ABSTRACT

A method for analyzing properties of a sample by measuring fluorescence parameters in multiple foci, comprises the steps of splitting a collimated primary laser beam with a splitting device into at least two collimated secondary laser beams and deflecting the secondary laser beams such that they propagate at different propagation angles with respect to an optical axis of a focussing optic, focussing the secondary laser beams with the focussing optic into at least two volume elements in the sample, detecting light emitted from the volume elements with a detecting device, and evaluating the detected light for obtaining the properties to be analyzed. Furthermore, a device for implementing this method is described. The invention is particularly suited for high-throughput screening applications.

19 Claims, 10 Drawing Sheets

MULTI-PARAMETER FLUORIMETRIC ANALYSIS IN A MASSIVELY PARALLEL MULTI-FOCAL ARRANGEMENT AND THE USE THEREOF

The present invention relates to a method and device by which laser-induced fluorescence is detected in a plurality of confocal volume elements in parallel in a sample volume and whereby from the flow of detected fluorescence photons time-resolved multi-parameter information about the sample is extracted, in particular about the biochemical composition the physical, chemical or spectroscopical properties, or the structure of biochemical or biological samples. The inventive method is particularly suitable for measuring high-resolution biochemical kinetics and for high-throughput screening applications.

BACKGROUND OF THE INVENTION

In the life sciences in general, and in biotechnology in particular there exists an extensive need for bioanalytical methods that enable the precise, fast and efficient analysis of chemical, biochemical end biological parameters in different sample formats, e.g. aqueous solutions, complex biochemical mixtures at the surface or in the interior of cells, or in specimens taken from plant or animal tissue.

The general task of such bioanalytical methods is the characterization of a biological or biochemical sample with regard to its chemical composition with a very high spatial and temporal resolution. Ideally, these methods allow the real-time analyses of the chemical composition of small, addressable volume elements and their change over time. The scale of such volume elements should be in the range of the microstructure of biological processes, i.e. the size of a cell and below. The temporal resolution should be in the order of the biological processes, i.e. in the range of microseconds and less. The sensitivity should be down to the single molecule level, because biological processes often rely on or are triggered by a single molecule. Moreover, populations of biological molecules—such as proteins—are obviously quite heterogeneous as can be seen from single molecule analyses, and this intrinsic heterogeneity seems to be quite important for the regulation of biological processes.

The use of fluorescence is extraordinarily well suited for such bioanalytical methods for a number of reasons. First, fluorescence is induced. Hence, molecules of interest can selectively be excited, thereby enabling to discriminate between different molecules and to suppress background. Second, fluorescence is a property of the single molecule, i.e. a single molecule can be excited and correspondingly emits single photons that can be detected. Therefore, fluorescence can be measured with single-molecule level sensitivity. Third, fluorescence parameters are characteristics of the nature of the molecule that undergoes fluorescence. The wavelength of photons that are absorbed, the lifetime of the excited state, the wavelength of emitted photons and the polarization angle of emitted photons are all characteristics of the chemical structure of the fluorescent molecule. These and more parameters can all be exploited to detect and discriminate different biomolecules. Fourth, fluorescence is fast. The lifetime of the fluorescent state is typically in the order of pico- to nanoseconds. Therefore, kinetics in the order of micro- to milliseconds can be resolved. Fifth, fluorescence is non-destructive and non-invasive and does not require any fixation of the specimen. Therefore, fluorescence can easily be analyzed in living cells or in tissue under mild conditions.

A number of bioanalytical methods that base on the measurement of fluorescence is known. In order to have a high spatial resolution, fluorimetry was rather early combined with confocal setups. The application of fluorimetry in a confocal setup in biotechnology was extensively demonstrated by Elgen and Rigler (PNAS 1994, 91(13):5740). Elgen and Rigler described in particular fluorescence correlation spectroscopy, which records correlations among the fluctuating fluorescence emission signal, and which thereby allows the analysis of molecular diffusion and transport phenomena. The authors used this technique for the measurement of molecular sizes and of biomolecular interactions such as the binding of a ligand to its receptor. Furthermore, they coupled these analyses with devices for trapping single molecules in electric fields, in order to increase the sensitivity and to decrease the detection limit further. In these measurements, molecules were labeled with specific fluorophores and could be monitored at concentrations of $10^{-15}$ M and less.

Problems of this and other setups are among others the limited spatial resolution, comparable long recording times in order to obtain very high data quality, the requirement for overlaying two or more laser beams in order to excite more than one fluorophor, and the difficulties of aligning the pinhole to restrict the open volume element in the axial direction.

Multi-photon excitation has been used to decrease the size of the volume element further and to clearly restrict the volume element without requiring any pinhole. The principles of two-photon excitation in combination with high resolution microscopy were described by Denk et al. (Science, 246 (1990) 73–76). Multi-photon excitation has several substantial advantages especially for the use with biological samples and methods based on molecular fluctuations in a microscopic focus. Two-Photon excitation is restricted strictly to the focal area of a microscope objective due to its non-linear nature. The result of this is a very high contrast, a very high spatial resolution, and no need to use a spatial filtering element ("pinhole") to confine the detection volume, which facilitates the alignment procedure. Further, problems such as photodestruction and photobleaching of the biomolecules or the marker molecules are reduced. Photodestruction and similar effects often lead to false or misinterpreted results.

A particular set-up for the use of two-photon excitation is described in WO 02/08732. Sample analysts marked by different fluorescent dyes having spectrally different fluorescence emissions are illuminated by one laser-wavelength by means of two-photon excitation. The fluorescence emissions are detected by two separate detection devices. The use of two-photon excitation ensures both, the identity of the excitation volumes for both dyes and avoids the use of a pinhole for the confinement of the measuring volume in both detection paths. The setup is, however, limited to cross-correlation and/or confocal fluorescence coincidence analyses, and reveals no spatial information.

Analyses with higher precision, higher sample throughput, and in addition spatial information about each sample, can be achieved when parallelizing these single-focus confocal fluorimetric setups. Preferably this can be done using setups with multiple foci.

Improved setups for fluorimetric analyses have been described that detect fluorescence in a multitude of volume elements. The patent specification U.S. Pat. No. 6,815,262 describes an apparatus and a method for carrying out laser-induced two-photon fluorescence correlation spectroscopy in parallel in a plurality of probe volumes. In this setup, a laser beam is consecutively focused via microscope objectives through a series of sample volumes, i.e. the light passing one sample volume is refocused into the next sample. Fluorescence is detected by a parallel arrangement of optical devices comprising lenses, filters and a photomultipiler for each sample. The setup is complex since it requires high quality optics for each focus. Furthermore, the excitation intensity decreases from sample to sample due to optical losses in the samples and optics alongside the serial arrangement. This leads to limitations when comparing resulting fluorescence signals from different samples. Furthermore, the setup generates foci in different samples. Therefore, the setup reveals no spatial information from the sample.

WO 01/40789 describes a setup for measuring fluorescence in a confocal setup in a multitude of focal points created in each sample. The technical set-up uses a multitude of optical fibers, a beam splitting device and focussing optics. The laser beam or any other light used for excitation is guided through a multitude of optical fibers. The output of fibers is directed via a dichroic mirror to a focusing optics which in turn is focusing the excitation light into a multitude of secondary fibers. The output of the secondary set of fibers is focused by another focusing optics into the sample creating a multitude of foci. The resulting fluorescence from molecules in the foci is then collected by the same optics into the secondary fibers. Then, after passing the dichroic mirror, the fluorescence is focused into a third multitude of fibers which finally directs the fluorescence light onto at least one detector device. To achieve diffraction limited high quality focal spots in the sample and confined detection volumes, which are essential for measurements based on molecular fluctuations, all fibers in the optical excitation path have to be monomode fibers. Besides the fact that the alignment procedure is very time consuming, the coupling of light into monomode fibers is subject to severe loss of intensity. This accounts for the excitation light as well as for the detected fluorescence, which lead to a significant reduction in the number of detected emission photons per excited molecule. In addition, this makes the setup incompatible with multi-photon excitation since the fibers cause a significant pulse-broadening of fs laser pulses, which are necessary for two-photon excitation. Using one-photon excitation in a multi-focal setup, however, leads to severe crosstalk between the foci due to excitation beyond the focal area, which further reduces the quality of the signal.

In summary, all the conventional setups described so far are limited in terms of their spatial and temporal resolution, their signal quality, their recording speed and therefore their sample throughput their robustness toward complex and changing sample matrices, and their technical stability and requirements for readjustments and alignments.

SUMMARY OF THE INVENTION

Therefore, the technical problem underlying the present invention is to provide an improved method for analyzing fluorescence parameters of a sample. A particular object of the invention is to provide a method for analyzing in particular biological or biochemical samples with high spatial and temporal resolution, with a high sample throughput, with a high robustness toward complex and changing sample matrices, and with a high optical stability and less efforts in aligning the optical setup. The setup should be broadly applicable, for a variety of fluorescent molecules and a maximum of fluorescence read-out parameters. Another object of the invention is to provide an improved device for analyzing fluorescence parameters of a sample.

According to a first aspect of the invention, a method for analyzing properties of a sample by measuring fluorescence parameters (or generally; parameters of the interaction between light and the sample) in multiple foci, comprises the steps of splitting a collimated primary (or first) laser beam with a splitting device into at least two collimated secondary laser beams and deflecting the secondary (or second) laser beams such that they propagate at different propagation angles with respect to an optical axis of a focussing optic, focussing the secondary laser beams with the focussing optic into at least two volume elements in the sample, detecting light emitted from the volume elements with a detecting device, and evaluating the detected light for obtaining the properties to be analyzed. According to a second aspect of the invention, a device for analyzing properties of a sample by measuring fluorescence parameters in multiple foci, comprises a source for generating the collimated primary laser beam, a splitting device for splitting the primary laser beam into at least two secondary laser beams, wherein the splitting device contains plane refractive or reflective surfaces being arranged for forming the secondary laser beams as collimated laser beams each of which having a different propagation angle with respect to an optical axis of the focussing optic, a focussing optic for focussing the secondary laser beams into at least two volume elements in the sample, and a detecting device for detecting light emitted from the volume elements and for evaluating the detected light in order to obtain the properties to be analyzed. By the combination of these measures, the foci in the sample can in particular be produced with high precision end improved homogeneity. Splitting the excitation light into collimated beams has the particular advantage of avoiding optical distortions in the optical setup.

In particular, the present invention is directed to a device and a device that enable the characterization of samples with high speed by measuring simultaneously, in a plurality of volume elements in each sample, laser-induced, multi-photon excited fluorescence with high spatial and temporal resolution. Main benefit of this multi-foci setup is that determination of molecular fluorescence parameters can be performed in parallel instead of subsequently. Therefore, measurement times can be shortened significantly. In addition, several molecular parameters can be analysed simultaneously in a sample and compared in real time, the method is particularly suited for performing fluorescence fluctuation analyses. Fluorescence fluctuation analyses are analyses that determine sample properties by evaluating fluctuations in the fluorescence signal. Such evaluation is preferably done by momentum analyses. The method allows therefore determination of molecular parameters like fluorescence lifetime, fluorescence anisotropy, fluorescence energy transfer, fluorophor mobilities, and their combinations in a multitude of foci. The setup reveals diffraction limited optical quality and is free from crosstalk between the foci in the same sample. Furthermore, the setup is compatible with a wide range of fluorescent molecules, preferably by tuning the excitation wavelengths to excite all fluorescent molecules of interest at the same time without the need of any alignment procedure or changing optical components. Further, the setup provides a homogeneous intensity distribution among the focal volume elements for wavelengths over a broad wavelength range.

For multi-photon excitation applications, the method of the invention comprises the following steps:

(a) generating the first laser beam with an intensity and wavelength that is suitable for multi-photon excitation;
(b) generating a plurality of two or more second laser beams with homogeneous intensities from the first laser beam;
(c) coupling the plurality of two or more second laser beams at different angles into the back aperture of a microscope objective forming the focusing optic, thereby generating a plurality of two or more illuminated volume elements in the sample volume;
(d) projecting the plurality of two or more volume elements by means of the same microscope objective and a beam splitter on a plurality of two or more detection units;
(e) transform the flow of detected photons in each detection unit into a signal stream over time; and
(f) converting and/or combining the signals collected from the plurality of volume elements at different time points and from different detection units into information about the sample in the sample volume.

The device for multi-photon excitation applications comprises in particular the following components:
a source for generating a first laser beam that is suitable for multi-photon excitation;
an arrangement of optical components for splitting the first laser beam into two or more second laser beams preferably with homogeneous intensities;
an arrangement of optical components for coupling the second laser beams at different angles into the back aperture of a microscope objective;
a microscope objective;
a beam splitter for separating fluorescence photons from the excitation radiation;
a focusing optics to project each volume element onto a detection unit, optionally via optical fibers;
two or more detection units, the number being equal to or a multitude of the number of second laser beams; and
a signal processing unit to transform detected photons into a signal stream, and to compute combinations and correlations of the signals from different volume elements at different time points.

According to the invention the plurality of volume elements are defined by a plurality of focal spots within the same sample volume. The multi-focal set-up is performed by an inventive arrangement of optical devices.

In a preferred embodiment of the invention, the technical set-up consists in the splitting of the laser beam into several individual beams by the use of an array of mirrors. In another preferred embodiment of the invention, the multi focus array is generated by the division of the one laser beam into individual beams with different angles by the means of an arrangement of prisms. In a particularly preferred embodiment of the invention, the multi-focal set-up is generated by a combination of an arrangement of prisms and an array of mirrors.

BRIEF DESCRIPTION OF THE FIGURES

Further details, advantages and preferred features of the invention are described in the following with reference to the attached drawings. The drawings are provided in order to explain further the present invention in supplement to the detailed description, but are not obstrued to limit the invention in any regard.

DETAILED DESCRIPTION OF THE INVENTION

In the framework of this invention the following terms and definitions are used.

"Counts Per Particle" is the average number of photons per second, emitted by a persistently re-excited single fluorescing molecule and cleared by a detection unit with consideration of all optical losses in an optical setup.

The term "volume element" is referred to the extracted volume within the sample volume with its dimension being defined by the inventive use of confocal optics. The "volume element" is the unit within the sample volume, at which the sample is illuminated by the second laserbeam generated by this invention. Fluctuation analyses evaluate signal fluctuations in such a volume element.

A "Confocal" setup is defined by an arrangement of optical components where the optical excitation and detection path is directed through one single lense or microscope objective thereby causing the focus of this lense or microscope objective being identical for the optical excitation and the optical detection path. This ensures that even with a volume element which is smaller as <1 µm in diameter the excitation volume and the detection volume within a sample is identical without any need for alignment to overlay those two volumes spatially.

"Illumination Intensity" is the intensity of electromagnetic radiation, which is finally illuminating the volume element considering all losses in an optical setup.

The present invention is directed to a method and a device that enable the characterization of samples with high speed by measuring simultaneously, in a plurality of volume elements in each sample, laser-induced, multi-photon excited fluorescence with high spatial and temporal resolution. The detected fluorescence photons are transformed into a signal stream that carries information about the location of the volume element from which each detected photon originated, the energy and the polarization angle of each detected photon, the life time of the excited state of each detected photon, and further parameters. The signal stream is evaluated in real time in order to reveal information about the structure and/or composition of the sample that is analyzed and the temporal evolution of these parameters.

Figure 1:
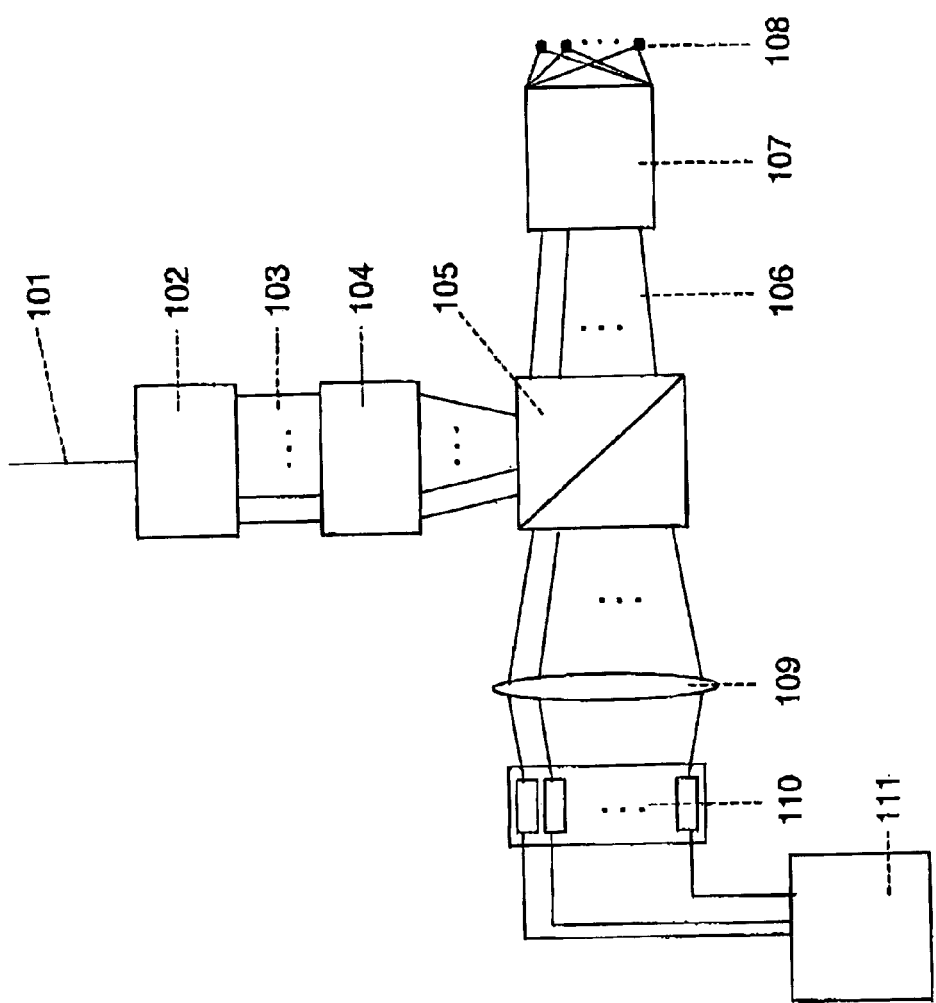
FIG. 1: depicts schematically the invention with the method and apparatus enabling measuring fluorescence parameters in a plurality of volume elements within the same sample volume defined by the plurality of focal points.

An embodiment of the invention, in particular a method being adapted for multi-photon excitation of the samples, is schematically illustrated in FIG. 1. Accordingly, a first laser beam 101 is generated that has a photon density and a wavelength which are suitable for Multi-Photon Excitation. By means of a beam splitting unit 102, this first laser beam is separated into a plurality of two or more parallel second laser beams 103, with a homogeneous intensity distribution among the second laser beams. The direction of the multitude of second laser beams is then modified by a deflection unit 104 in order to generate laser beams with different angles 106. Via a beam splitter 105, these laser beams are then coupled into the back aperture of a microscope objective 107, thereby generating a multitude of two or more illuminated volume elements 108 in the sample volume. The photon density in each of the volume elements is set as high as required for Multi-Photon Excitation, and fluorophores residing in or passing through the volume element are excited to their fluorescent state. The volume elements are then projected via a focusing optics 109 onto a detector set 110 which, in combination with a signal processing unit 111, enables the time-resolved detection of photons, their allocation to any of the employed volume elements, and their characterization with regard to the photon energy, the duration of the excited state, the polarization angle and further characteristics. By means of the signal processing unit 111, this information is further processed in order to reveal information about the structure and composition of the sample that is analyzed and the temporal evolution of these parameters. Therefore, the method is particularly suited for measuring chemical or biochemical reactions, such as ligand-receptor binding, enzyme kinetics or similar kinetics. Moreover, the method is particularly suited for measuring molecular transport processes.

The use of Multi-Photon Excitation in confocal fluorimetry offers several benefits over Single-Photon Excitation. First, multi-photon excitation is restricted strictly to the focal area due to its non-linear nature. A consequence is the elimination of the problematic so-called "cross-talk" between different foci in a sample. As the excitation is negligible outside the focal volume, interferences by fluorescence from out-of focus background of the diverse adjacent excitation and detection volumes do not exist. Therefore the important parameter Counts Per Particle is not compromised in the multifocal setup, as it typically is when using one-photon excitation. Multi-Photon Excitation also avoids the use and time-consuming alignment of individual pinholes for each focus as necessary for one-photon setups to further confine the detection volume. In combination with the large detection area of the employed detectors, Multi-Photon Excitation enables a very high alignment stability.

Another important advantage of Multi-Photon Excitation refers to the possibility to excite simultaneously several fluorescent molecules that differ significantly in their one photon absorption spectra. Multi-Photon Excitation is capable to excite all common fluorescence dyes and fluorescing proteins, since their two-photon cross-section spectra have a significant amplitude in the range of common tuneable lasers. Even if the emission spectra of excited fluorescent molecules are quite different, typically a common two-photon excitation wavelength can be found, since their two-photon cross-section spectra overlay significantly. As a further consequence, there is no requirement to overlay the excitation volumes of different lasers by time-consuming alignment processes. Another advantage of Multi-Photon Excitation is that, in general, the requirement for changing filters or dichroic mirrors and subsequent time-consuming re-alignment of the system when using different fluorescing molecules is dispensable. One filter and one dichroic mirror-set can generally be used to prevent photons of the infrared excitation-source to hit the detectors which are supposed to detect only photons. In the visible range where the wavelength, of fluorescence photons emitted by the fluorescing molecules lies.

Another advantage of Multi-Photon Excitation is the high quality of the resulting focal spots with respect to the shape of their excitation profiles which is close to a sphere. A consequence of this is that even for read out parameters which strongly depend on the shape of the focal volume element, e.g. molecular brightness, the optics for the creation of the excitation and detection volume has not to be changed in a time consuming procedure as it is typically required in the case of Single-Photon Excitation.

In order to achieve reasonable Multi-Photon Excitation, a high peak power of the electromagnetic field is needed. According to the method of the invention, this is achieved by employing pulsed laser sources as sources for the first laser beam (101). Preferably, high-repetition femtosecond pulsed lasers having repetition rates in the range of 100 MHz and pulse durations in the range of 100–300 femtoseconds are used. These laser sources provide very high peak powers while stiff being insensitive to pulse broading which may be due to dispersion effects in the optics of a confocal setup. The high repetition rate in the range of 100 MHz allows a maximum rate of subsequent excitations of the fluorescing molecules since the corresponding period of 10 ns is well above the relaxation time of most of these molecules which is in the range of 0.5 to 5 ns. However, when the analysis is based on molecular states, which typically have even shorter lifetimes than 0.5 ns, e.g. states with typical lifetimes on the ps or fs time scale, even significant higher repetition rates of the excitation pulses than 100 MHz are preferred. Therefore, the invention preferably employs a wavelength-tunable light-source providing linearly polarized ultra-short laser-pulses. In the near infrared, e.g. Titan-Saphir fs-light-sources. The use of light in the infrared region is advantageous for excitation of most common fluorescent molecules via two-photon excitation. A further advantage in the use of femtosecond pulses is the possibility to simultaneously measure dynamics on the picosecond (e.g. fluorescence lifetime) and femtosecond timescales (e.g. vibrational redistribution of fluorescent molecules). The excitation can also be done by circularly and/or linearly polarized laser light.

A pulsed laser source is also employed in the inventive setup in order to enable the measurement of the duration of the excited state for any detected photon. By means of a signal processing unit, the time-resolved signals from the detection unit are combined with a trigger signal from the pulsed laser source to extract information about the distance between the Two-Photon Excitation event and the emission of the corresponding fluorescence photon.

According to the method of the invention, the collimated laser beam generated by a suitable laser source is preferably widened to the size of the back aperture of a high quality microscope objective or a multiple thereof and then separated or splitted by a set of optical components 102 into a multitude of secondary individual beams 103, which are eventually guided into a multitude of focal points within the sample volume by the inventive arrangement of optical devices.

According to the invention the secondary laser beams have identical intensities even if the wavelength is tuned over a broad range. The intensities of the beans are regarded as identical when the measurable differences are smaller than 5–10% of the mean of the intensities of the plurality of the beams. A wavelength range is regarded as broad when it covers at least 100–200 nm, The beams are next deflected by a set of optical components 104 in a way that all secondary beams overlay in the back aperture of a microscope objective 107, each entering into the objective at a slightly different angle 106). The multitude of non-parallel but collimated laser beams is then reflected by a beam splitter 105 that is able to discriminate between the—longer wavelength excitation light and the shorter wavelength emission photons. Thus, the beam splitter 105 is typically a dichroic mirror, but may also be a polarization cube, an intensity beam splitter, or a similar optical component.

The multitude of diffraction-limited excitation spots in a sample is generated using a high quality microscope objective 107. According to the invention the positions of the individual foci in the sample 108 are determined by the incident angle of the individual beams that enter the back aperture of the microscope objective. The size of the foci is typically in the range of <1 μm, but maybe significantly smaller or larger. The positions and distance between the foci can by adjusted as desired by the inventive arrangement of optical devices. Typically foci to foci distances are preferably in the order of 5 to 50 μm, more preferably between 10 and 20 μm, but car range from a fraction of the diameter of each focus up to the limit of the focusing optic. When using typical high quality microscope objectives this limit is between 300 and 1000 μm. The number of foci is also not limited and depends solely on the optical component 102. Depending on the embodiment the number of foci is either proportional to the number of optical components 102 or is even as high as $2^n$ or less, where n is the number of optical components 102.

Preferably, the number of foci is between 2 and 10000, more preferably between 2 and 1000, and most preferably between 2 and 100.

The fluorescence photons emitted by molecules that are excited when residing in or passing any of the volume elements, are collected by the same microscope objective 107. Due to the nature of the beam splitter 105 as described above, the fluorescence photons pass the beam splitter 105 and are refocused onto a detection unit 110. This detection unit comprises several detection areas. These detection areas can be sensitive areas of individual detectors, e.g. photo diodes, in particular APD's, or partitions of the sensitive area of detection arrays, such as CCD chips, or similar detection devices.

Preferably, the detection unit 110 has to provide enough sensitivity to detect single photons hitting the sensitive areas of the detection unit. Whenever photons are detected in a sensitive area of the detection unit, a signal corresponding to the address of the volume element from which the photon originated, the wavelength and/or the polarization angle of the photon and further parameters are extracted by a signal processing unit 111.

Figure 2:
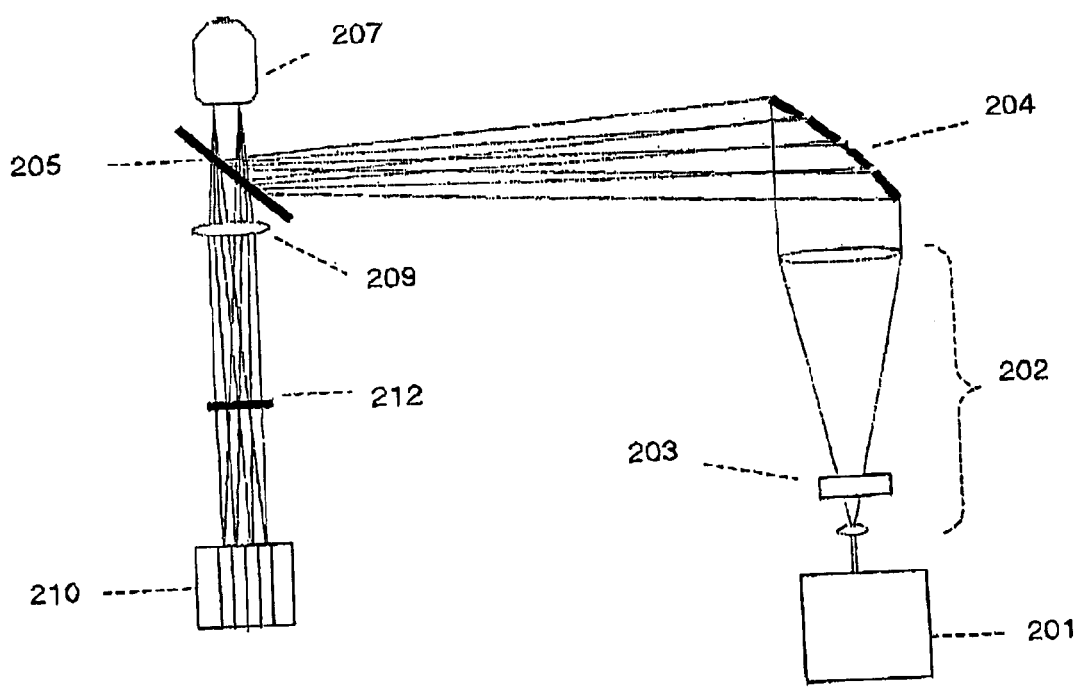
FIG. 2: depicts schematically embodiment A of the invention whereby the generation of a multi focus array is realized by a mirror array.

The inventive method can be realized by one of tile following embodiments. In a first embodiment (Embodiment A, FIG. 2), the generation of the collimated beams having different incident angles is achieved by an arrangement of flat mirrors. In this case the collimated laser beam generated by the source (201) is widened to the size of the entire array of flat mirrors by means of a beam expander (202) and then modulated by means of a beam shaping element (203). The tilting angle of the mirrors can be, in turn, adjusted individually to direct the individual collimated beam by an individual mirror to the back aperture of the microscope objective. According to the invention the exact position of the corresponding focus in the sample can the be governed by the tilting angle of the mirror. Therefore also the exact focal position in the detection path, which is described below, can be determined by the tilting angle of the mirror. According to the invention this avoids an individual alignment of the detectors or detector fibers (210) in the detection path. This facilitates the initial alignment of the system in a very advantageous way. The optical quality of the foci created in this way is very high, since the beam-profile of the individual beams is very close to a so-called "flat top" shape and the wavefront of the beams is very flat.

Figure 3:
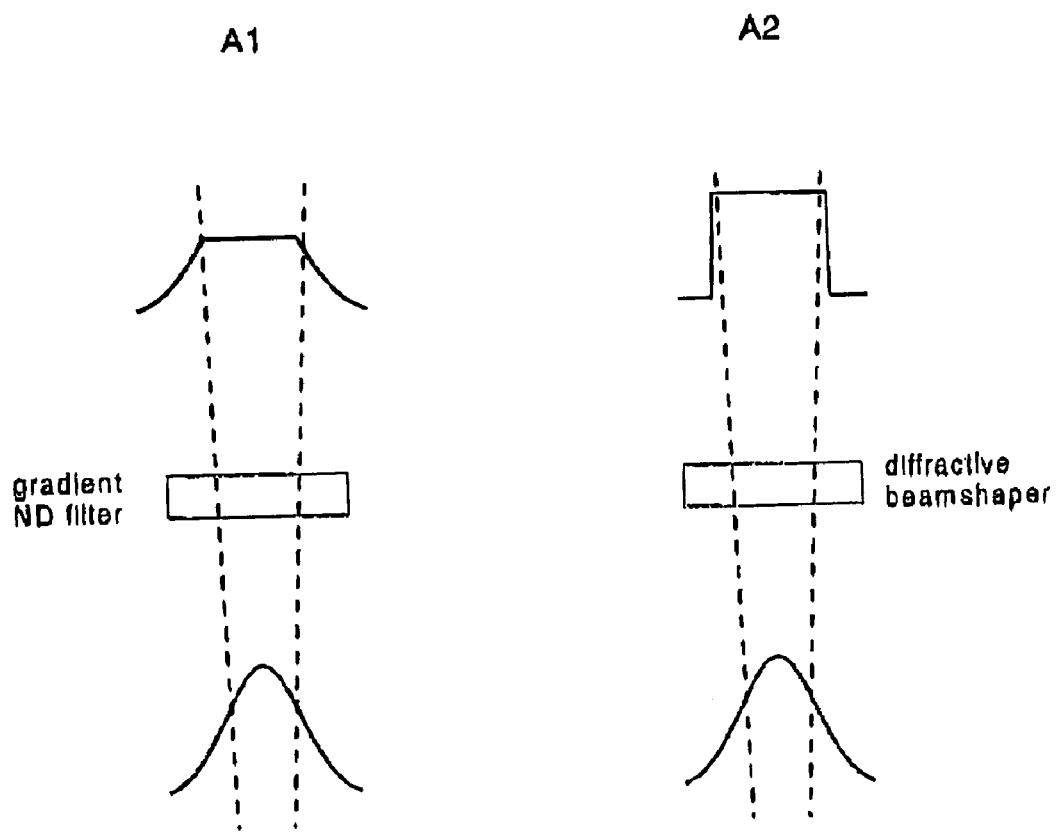
FIG. 3: shows the use of beam shaping elements, embodiment A1 uses a gradient ND filter and embodiment A2 uses a diffractive beamshaper.

In a preferred embodiment of the invention (Embodiment A1, FIG. 3), the gaussian intensity profile of typical laser sources is changed using a gradient neutral density filter in order to achieve homogeneous excitation intensities in each focus. The gradient neutral density filter has a centrosymetric inverse gaussian profile of the optical density. The maximum optical density is therefore in the center of the filter where the maximum intensity of the laser beam occurs. The optical density at this point, however, is only as dense that still a significant part of the light can pass. In the same way, the intensity of the beam is decreasing away from its center the optical density of the filter is decreasing. The resulting intensity profile after the filter is flat in a central region of the original gauss profile. This region is then used to illuminate the mirror array homogeneously.

In a second preferred embodiment of the invention (Embodiment A2, FIG. 3), a diffractive beam shaper is used as the beam shaping element in order to achieve homogeneous excitation intensities in each focus. An diffractive beam shaper is a special case of a diffractive element (Turunen and Wyrowski, Eds., in: Diffractive Optics for Industrial and Commercial Applications, Akademie Verlag, Berlin, 1997). Unlike lense and mirrors, the function of diffractive elements is based on scattering and interference. A diffractive element is usually a thin flat substrate. On one side of the component there is a fine groove structure. Diffractive optics shapes light by exploiting its wave nature. The advantage of using a diffractive beamshaper over using the gradient neutral density filter is that there is no loss of the laser intensity. Diffractive beamshapers, which are know to person who are skilled in the art, are using interference effects to create any desired diffractive pattern from a beam with known properties. The preferred diffractive pattern used for this embodiment of the invention creates a so called "flat top" pattern from the incoming beam, which distinct feature is a homogeneous, rectangular intensity profile. Therefore each mirror can be illuminated homogeneously.

Figure 4:
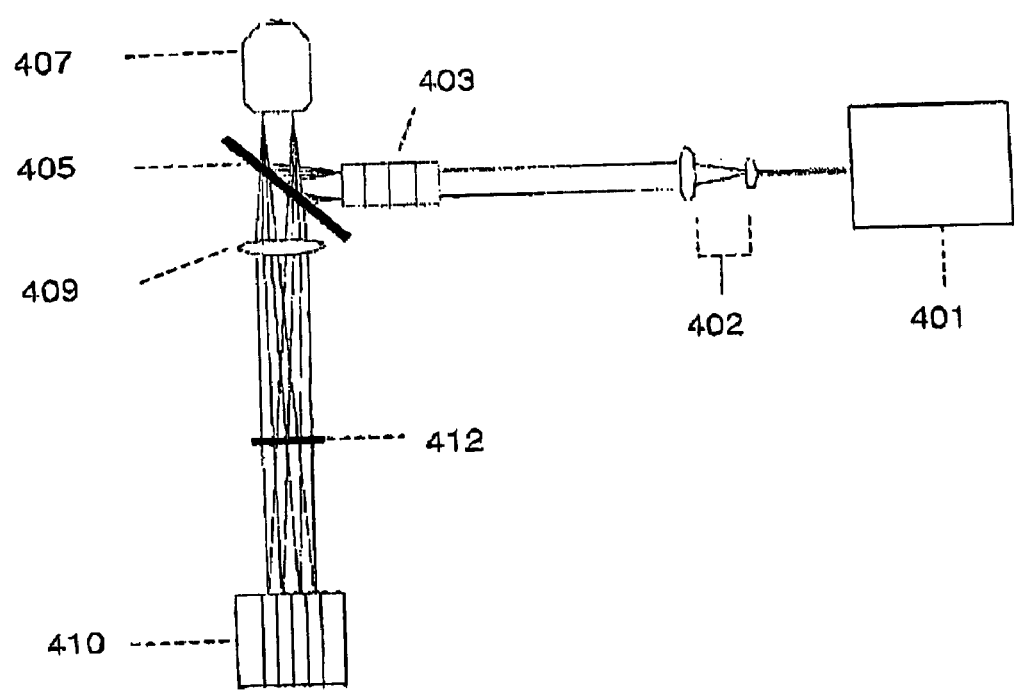
FIG. 4: depicts schematically embodiment B of the invention whereby the generation of a multi focus array is realized by a set of Wollaston prisms.

In a further embodiment of the invention (Embodiment B), the multi-focus array is generated by means of prisms. FIG. 4 shows schematically a preferred technical set-up of this embodiment. The laser beam provided by the source (401) is expanded to the size of the back aperture of the high quality microscope objective (407) and then guided to a set of prisms (403). By the use of polarization prisms the laser beam is spill into a multitude of beams with the absolutely identical high quality beamprofiles and energies but with different propagation angles. Preferably, the division of the one laser beam into several single beams with different angles is accomplished by a set of Wollaston prisms. According to the invention an intrinsic feature of prisms is used, which consists in the separation of a laser beam of linear polarized light into two beams with orthogonal polarization angles which are identical despite the polarization when the polarization of the incoming beam is filtered by 45° with respect to the two orthogonal polarizations of the two outgoing beams of the prism. According to the invention n prisms can be arranged in an array with alternating relative angles of the main axis of 45° for the generation of $2^n$ identical beams with alternating polarization. This enables the creation of an exponential increasing number of identical beams with only a linear increase of the number of used prisms n. In t a preferred embodiment these outgoing beams have only slightly different propagation angles of typically less than 1°. Therefore, in this embodiment the set of Wollaston prisms serves as the beam splitting (102) and the deflection unit (104) in combination.

Figure 6:
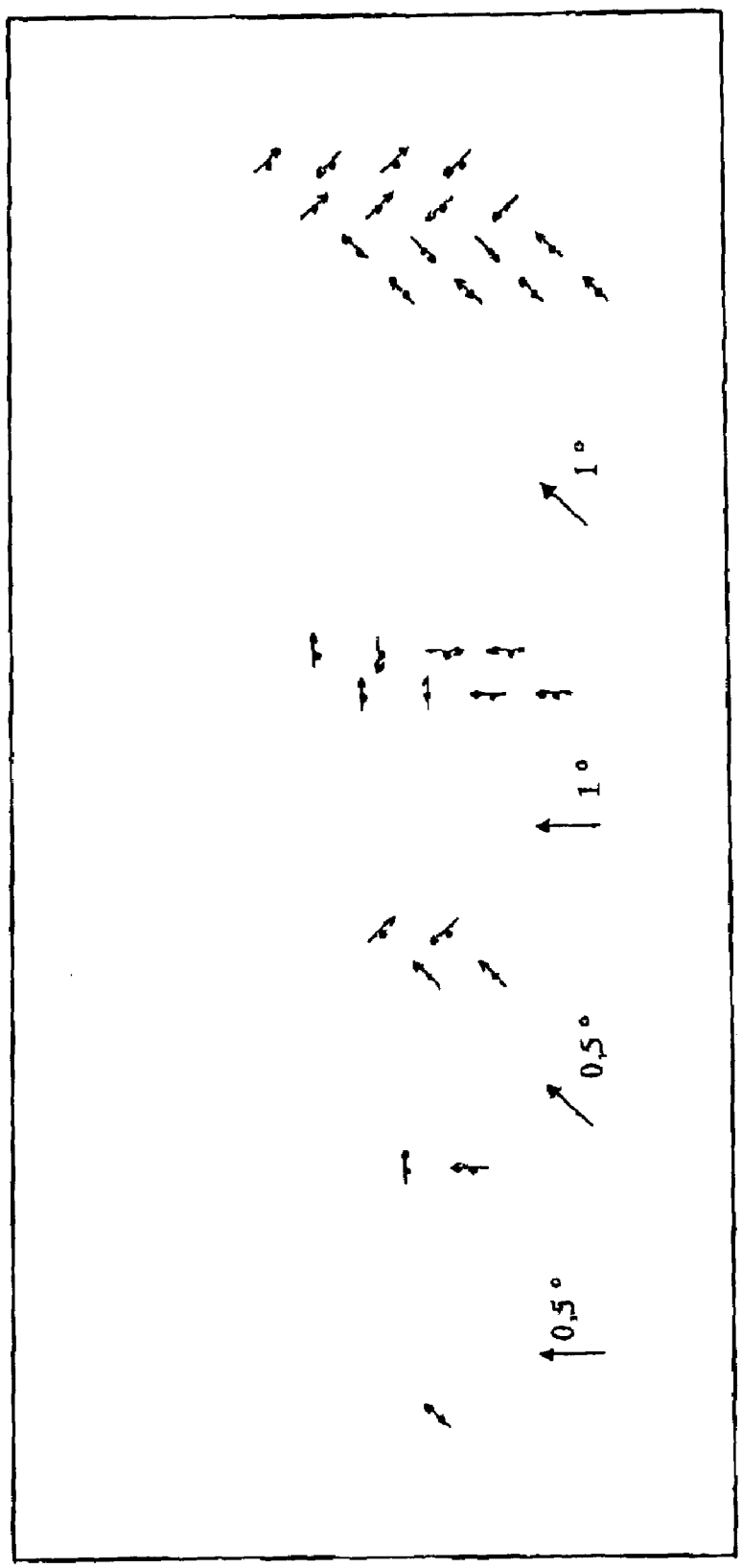
FIG. 6: shows the pattern of focal points generated by the inventive application of 4 Wollaston prisms.

In a particularly preferred embodiment (Embodiment B1), the Wollaston prisms are arranged to achieve a rhombus-shaped focal array. An example of such an arrangement with four Wollaston prisms is shown in FIG. 6. The first Wollaston prism is oriented towards tile expanded linear polarized laserbeam in a way (tilting angle 45°), that the beam is split into two new beams with orthogonal linear polarizations which deviate + and −45° from the original polarization. This is repeated for the two new beams with a second Wollaston prism which in turn again spills the two beams into four new beams. The next Wollaston prism again splits the four beams into 8 beams but this time the splitting angle of the propagation vectors of the beams is half the amount of the splitting angles of tile first and the second Wollaston prism to avoid recombining of beam vectors. According to the invention there are a multitude of possibilities for relative orientations and splitting angles of the prism assembly to yield well separated beams of the same quality and energy and also different energies.

The outgoing beams of the array then are directed towards a focussing optic, e.g. the back aperture of the microscope objective, creating identical high quality focal spots at different positions in the sample according to their different incident angles. When using Wollaston prisms the deviations of the centers of the incoming beams from the center of the back aperture of the objective are extremely small and do not compromise the quality and uniformity of the foci since the angles are typically less then 1°.

Figure 5:
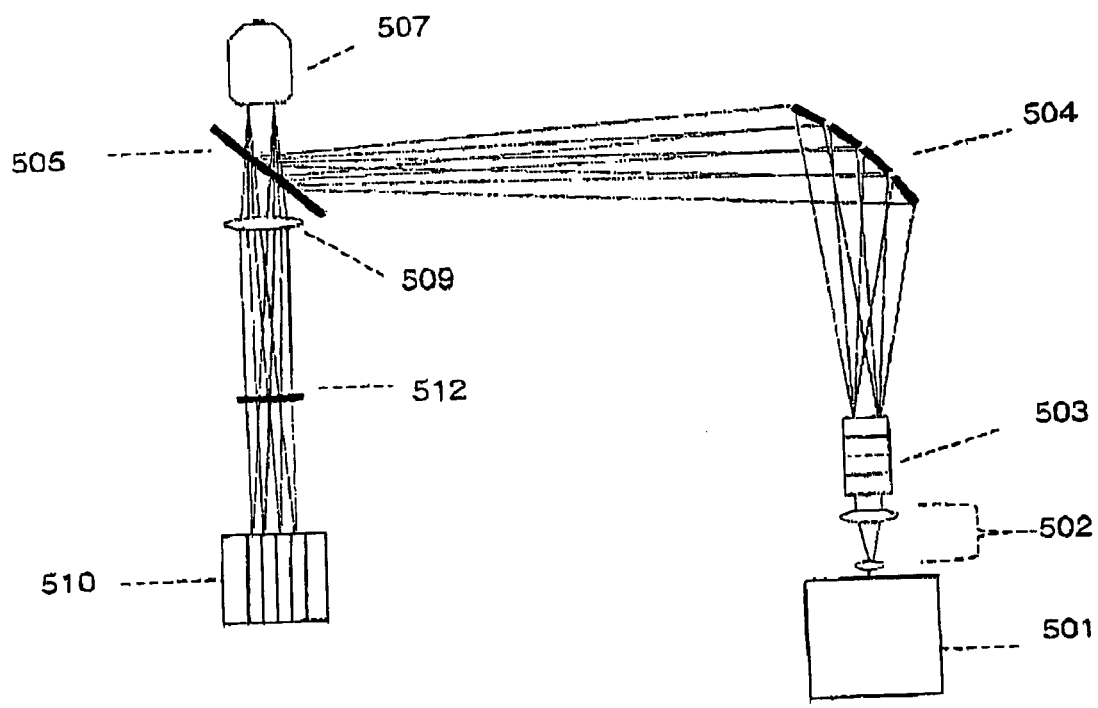
FIG. 5: depicts schematically embodiment C of the invention whereby the generation of a multi focus array is realized by a combination of Wollaston prisms and a mirror array.

In a further, particularly preferred embodiment (Embodiment C) the multi focus array is generated by the combination of the technical set-up of prisms and fiat mirrors. A preferred technical set-up of this embodiment is shown schematically in FIG. 5. Here, the outgoing beams of the array of prisms (503) hit mirrors of a mirror array (604) and are then directed by tilting the individual mirrors in the mirror array. Preferably, Wollaston prisms are used as the beam splitting prisms (503). This setup combines the advantages of both individual setups without any drawback. In particular, the small deviations of the centers of the incoming beams of the prisms from the center of the back aperture of the objectives in the preferred embodiment B—can be compensated by tilting the mirrors in such a way that all beams are combined exactly at the back aperture of the objective. Also the identical foci in the sample can be positioned in any desired way by tilting the individual mirrors. Therefore, in this embodiment the set of prism (503) serve as the beam splitting unit (102) and the mirror array (504) serve as the deflection unit (104). Due to the properties of Wollaston prisms. In such a setup no beam shaping element is required.

According to the invention, the detection unit (110) is arranged in a way that allows the time-resolved detection of single photons originating from each of the multitude of volume elements. Fluorescence light emitted by the fluorescing molecules at the foci in the sample is collected by the microscope objective and creates at the back aperture outgoing beams with the same small deviations in the propagation angles as the incoming excitation beams created by the inventive setup. They pass the dichroic mirror (105) known from state of the art confocal techniques and are focused at a position depending on the properties of the microscope objective or additional focussing lenses known to persons skilled in the art. At the position of the foci at least one detector is placed to detect the intensity or single photons of the emitted fluorescence light. In a preferred embodiment one detector is detecting all fluorescence of the individual foci. In a especially preferred embodiment of this type the detector is capable of single photon counting and has a high time resolution of <1 ns. In this especially preferred embodiment the one detector can distinguish photons coming from different foci by identifying characteristic different arrival times associated with the individual foci. In another preferred embodiment the fluorescence of individual foci is detected by an array of detectors. One preferred embodiment of this type is a high sensitive CCD (charged couple device) which can detect and resolve more than to 1000×1000 foci at the same time. Another preferred embodiment of this type is an array of photomultipilers or avalanche photo diodes (APDs) having individual detectors placed at the positions of the focussed fluorescence of the individual foci created in the sample and being able to resolve the arrival times of single photons by better than 1 ns. Another preferred embodiment is an array of cleaved or polished fiberends of fibers which in turn guide the collected fluorescence light in the individual detectors.

In the inventive method, the signal processing unit (111) is employed to extract information about the structure and composition of each example that is analyzed and the temporal evolution of these parameters with high speed and high resolution. This is realized by a combination of several signal processing modules. As described above, each individual detector of the detection unit generates a time-resolved stream of electronic pulses corresponding to the stream of photons hitting this detector. These single photon counting signals from the detectors are split into two electronic devices. One device is a standard electronic OR-gate, the Output of the OR-gate is the time-resolved sum of all electronic pulses created by all detectors for the individual foci. The other device is a binary decoder. The output of the binary decoder is a—the address of the selector where a photon was detected at the time the electronic pulse was created. Both outputs are connected to a ps time analysator which calculates distances between electronic pulses and laser trigger signals.

Since there is no deadtime connected to the detection of a single counting event in this type of device, this electronic evaluation is capable of evaluating photon count burst rates of up to several GHz and can evaluate counts from more than 200 detectors at the same time with a time resolution of better than 300 ps. Therefore an individual evaluation of the fluorescence lifetime or photon arrival times measured in a very large number of foci is enabled with ps-time resolution by this method. Also all other confocal methods based on the fluctuations of molecules and other methods based on fluorescence can be evaluated for each focus with this device individually. Also the individual arriving times of the photons can be connected to other measurable parameters or their combinations for each individual photon. The plurality of loci and the fast electronic acquisition also allow to extract information about the structure of the sample.

EXPERIMENTAL SECTION

EXAMPLE 1

Figure 7:
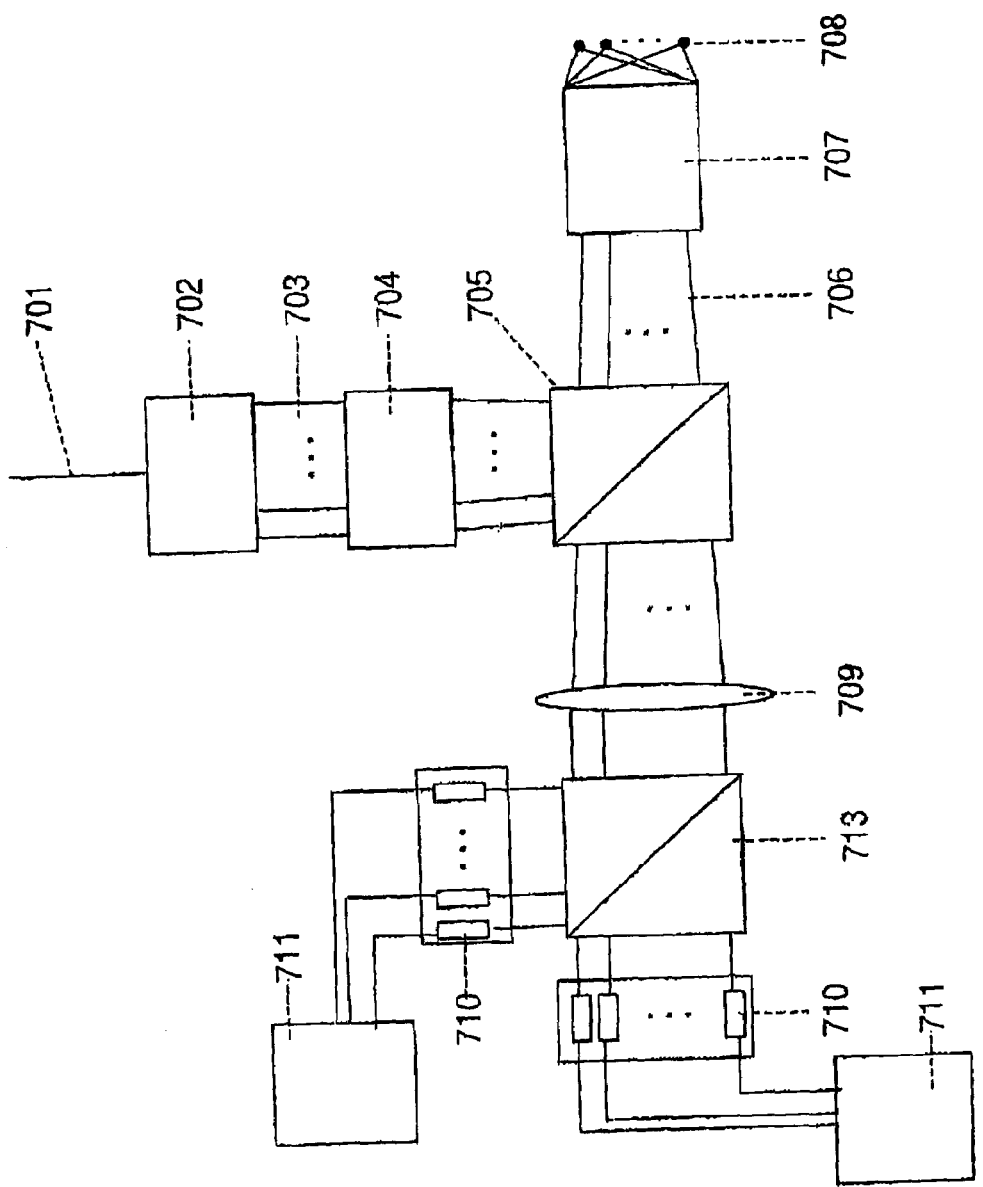
FIG. 7: depicts a particular setup with an additional beamsplitter that is used to split the fluorescence light equally onto two coincidence channels.
Figure 8:
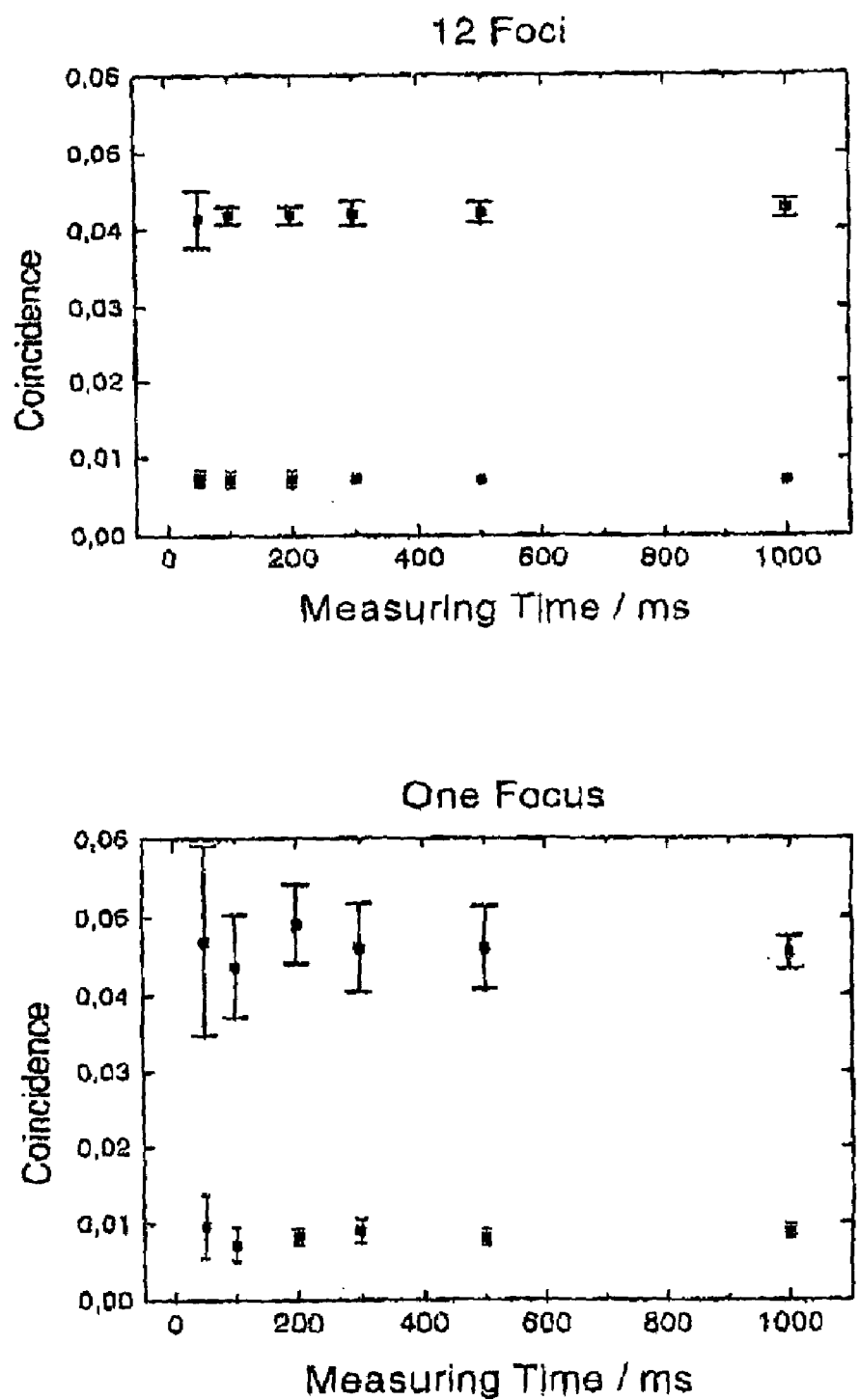
FIG. 8: shows the measurement of the coincidence value and its standard deviations of Tetramethylrhodamine (TMR) solutions using a beamsplitter which splits the fluorescence intensity equally onto two channels, shown is a comparison of a 12 foci setup with the same measurement in a 1 Focus setup at different measuring times.

In a first experiment, confocal fluorescence coincidence analysis is used to demonstrate the high precision of the method of the invention. The particular setup for this example is shown in FIG. 7. A beamsplitter (713) was used to split the fluorescence light equally onto both coincidence channels. Tetramethylrhodamin (TMR) solutions were used at concentrations of 20 and 100 particles per focus. Two-Photon Excitation was done at a wavelength of 830 nm. The measurements were performed at 1000, 500, 300, 200, 100 and 50 ms, respectively. Shown is the comparison of results obtained using one focus compared to 12 foci simultaneously (see FIG. 8). Standard deviations were determined from 3 measurements and are shown as errorbars. The plot clearly demonstrates that the multifocal setup allows the reduction of the measuring time by a factor that is proportional to the amount of foci while maintaining the same standard deviation. The standard deviation of the 100 ms measurement using the multifocal set-up is even bettor than the standard deviation of the 1000 ms measurement using one focus. Especially at very short times, when statistical fluctuations come into play, the results are a lot more accurate with the multifocal setup. Measurements can be performed well with measuring times lower than 100 ms, at which the single focus set-up shows an unacceptable high statistical error.

It clearly can be seen that the multifocal setup allows the reduction of tie measuring time by a factor proportional to the amount of foci while maintaining the same standard deviation.

EXAMPLE 2

With a similar multiphoton, multi-focal set-up comprising 8 foci, the mean particle number and the CPP are shown in Table 1. Again, Tetramethylrhodamine in combination with an excitation wavelength of 830 nm was used. As can be seen from this table, the obtained results show a high uniformity. The measured CPP of roughly 20 is close to the saturation value obtainable with the employed APD defectors. This value can be increased further when using stapilleators protecting the dye from photobleaching. The CPP value is then about 50 CPP which is very close to the values obtainable with one-photon excitation.

TABLE 1

| Focus | CPP | Particle Number |
|---|---|---|
| Average | 21.05 | 7.60 |
| 1 | 21.48 | 6.45 |
| 2 | 21.04 | 7.61 |
| 3 | 23.22 | 7.36 |
| 4 | 18.64 | 7.62 |
| 5 | 22.24 | 7.97 |
| 6 | 21.27 | 7.63 |
| 7 | 21.71 | 8.83 |
| 8 | 18.79 | 7.28 |

EXAMPLE 3

Figure 9:
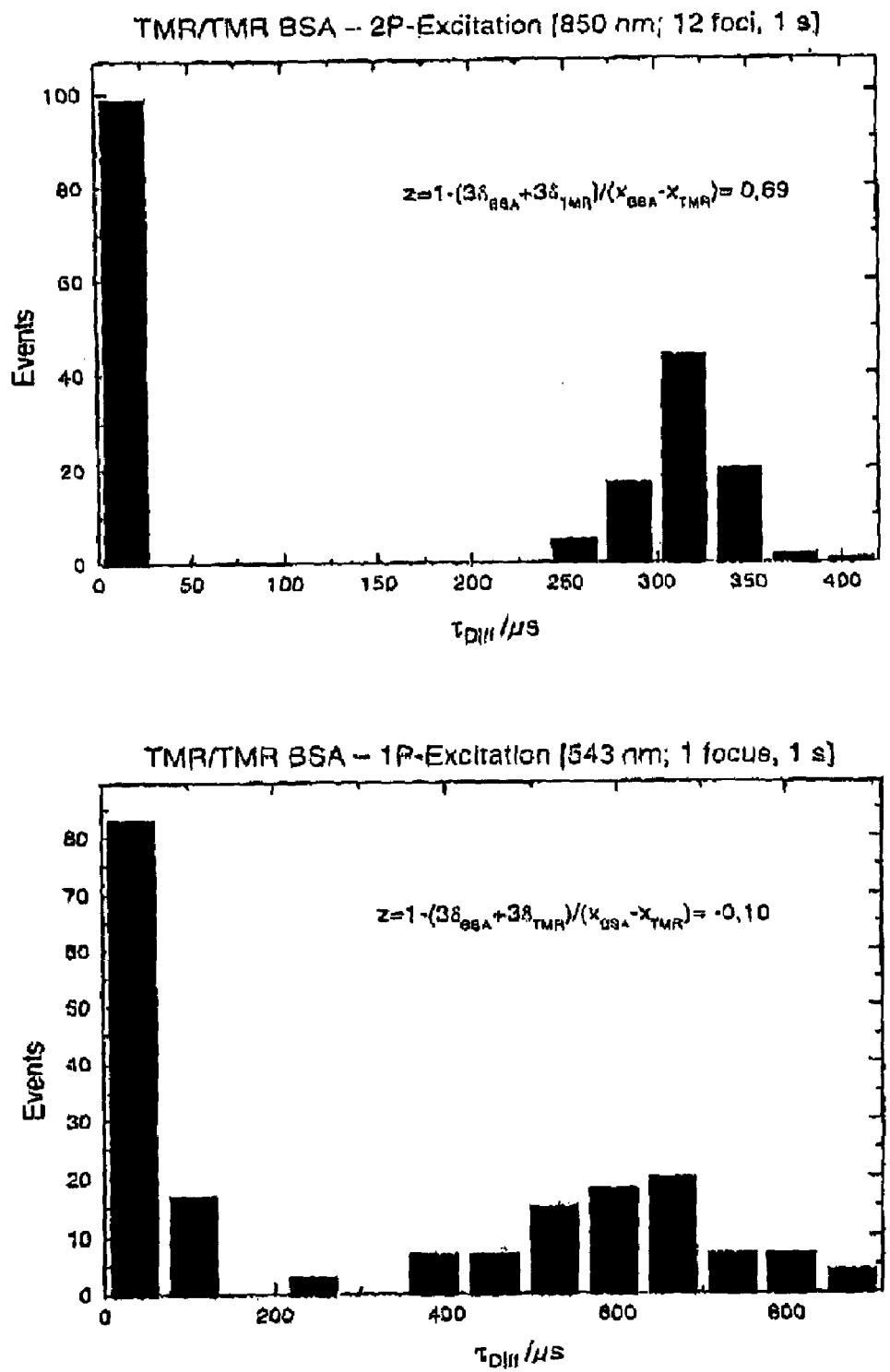
FIG. 9: shows a comparison of the z-factor or a one-focus, one-photon measurement of the diffusion time of TMR compared with TMR-labelled bovine serum albumine (BSA) with the same measurement in a multifocal two-photon setup.

In order to elucidate the influence of the lower CPP obtained with two-photon excitation for fluctuation analysis a measurement using one-photon excitation was compared with the same measurement using two-photon excitation. Tire diffusion times of the free TMR dye and the TMR-labeled protein Bovine Serum Albumine (BSA) were measured and the z-factor was calculated for both excitation options. For the one-photon excitation the excitation wavelength was 543 nm and the excitation power was approximately 100 μW. For two-photon excitation the excitation wavelength was 840 nm and the excitation power was approximately 30 mW at pulsewidths of about 200 fs and a repetition rate of 90 MHz. In all measurements the measured particle number was adjusted to 5 particles per focus. The z-factor was calculated as $z=1-(3\sigma_{TMRBSA}+3\sigma_{TMA})/(X_{TMABSA}-X_{TMA})$. Here $X_{TMRBSA}$ and $X_{TMR}$ denote the mean value of 100 measurements of the fitted diffusion time measured in a FCS experiment of a sample with TMR-labeled BSA and TMR. respectively. $\sigma_{TMRBSA}$ and $\sigma_{TMR}$ are the standard deviations of the corresponding mean values. The results are shown in Table 2. The z-factor is a measure for the suitability of an biochemical assay to discriminate between two assay endpoints. An assay with a z-factor above 0.5 is usually regarded to have sufficient resolution. As can be seen from table 2, the assay using 2-photon excitation in one focus is only performing slightly worse than using one-photon excitation in one focus. However, the z-factor of a one-focus, one-photon measurement is significantly worse than the same measurement of a multifocal (12) two-photon set-up. The z-factor of the multi-local multi-photon measurement shows the feasibility of this detection technique for determining biomolecular parameters. These results are further depicted in FIG. 9.

TABLE 2

| Experiment | $\tau_{Diff}$[TMR] | $\tau_{Diff}$[TMRBSA] | $z = 1 - \dfrac{3\delta_{BSA} + 3\delta_{TMR}}{x_{BSA} - x_{TMR}}$ |
|---|---|---|---|
| 1P Excitation [543 nm, 1 focus] | 64.45 ± 5.34 | 659.89 ± 213.46 | −0.10 |
| 1P Excitation [543 nm, 12 focl] | 63.86 ± 1.52 | 669.00 ± 34.83 | +0.82 |
| 2P Excitation [850 nm, 1 focus] | 23.24 ± 2.72 | 301.14 ± 104.76 | −0.16 |

TABLE 2-continued

| Experiment | $\tau_{Diff}$[TMR] | $\tau_{Diff}$[TMRBSA] | $z = 1 - \dfrac{3\delta_{BSA} + 3\delta_{TMR}}{\bar{x}_{BSA} - \bar{x}_{TMR}}$ |
|---|---|---|---|
| 2P Excitation [850 nm, 12 focl] | 23.48 ± 2.57 | 314.69 ± 27.86 | +0.69 |

EXAMPLE 4

Figure 10:
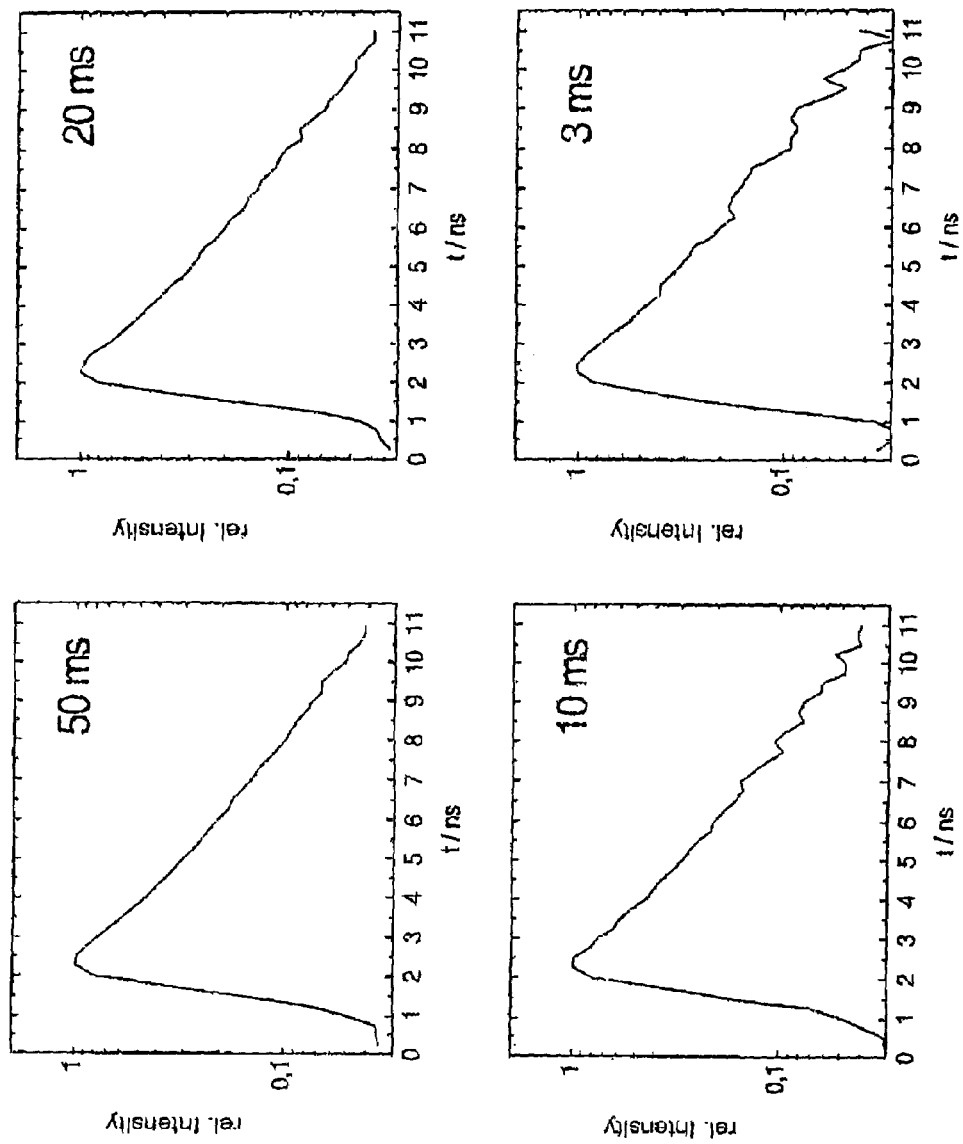
FIG. 10: shows fluorescence lifetime analyses of TMR measured with the inventive multifocal setup.

FIG. 10 shows lifetime analyses of TMR that are measured with the multifocal setup. Even at shortest measuring times, the quality of the curves is very high. The instrument response time that was achieved is lower than 500 ps which is close to the time resolution of the APDs used in these experiments.

What is claimed is:

1. A method for analyzing properties of a sample by measuring fluorescence parameters in multiple foci, said method comprising the steps of:
    splitting a collimated primary laser beam with polarization prism of a splitting device into at least two collimated secondary laser beams and deflecting the secondary laser beams such that the secondary laser beams propagate at different propagation angles with respect to an optical axis of a focusing optic;
    focusing the secondary laser beams with the focusing optic into at least two volume elements in the sample;
    detecting light emitted from the volume elements with a detecting device;
    evaluating the detected light for obtaining the properties to be analyzed; and
    generating a signal for displaying and/or recording a representation of the analyzed properties.

2. The method according to claim 1, wherein the at least two secondary laser beams have identical intensities, peak intensities and/or beam profiles at a plurality of wavelengths.

3. The method according to claim 1, wherein the splitting step comprises a broadening of the primary laser beam to provide a broadened primary laser and directing the broadened primary laser onto a mirror array reflecting the secondary laser beams.

4. The method according to claim 3, wherein the primary laser beam is subjected to a profile shaping by a neutral density filter or a diffractive beam shaper.

5. The method according to claim 1, wherein the secondary laser beams are generated with at least one Wollaston prism.

6. The method according to claim 5, wherein the secondary laser beams are directed from the at least one Wollaston prism to the focusing optic via a mirror array.

7. The method according to claim 6, wherein mirrors of the mirror array are selectively tilted for adjusting the propagation angles of the secondary laser beams.

8. The method according to claim 1, wherein the primary laser beam is generated with an intensity and wavelength suitable for multi-photon excitation of the sample and the focusing step comprises a multi-photon excitation of the sample in the at least two volume elements.

9. The method according to claim 1, wherein the focusing optic is a confocal focusing optic and the detecting step comprises projecting the at least two volume elements with the focusing optic and a beam splitter on corresponding detector units of the detecting device.

10. The method according to claim 1, wherein the detecting and evaluating steps comprise transforming a flow of detected photons in the detecting device into a signal stream over time and/or converting and/or combining the signals collected from the volume elements at different time points and from different detection units into information about the sample.

11. A device for analyzing at least one property of a sample by measuring fluorescence parameters in multiple foci, said device comprising:
    a source for generating a collimated primary laser beam;
    a splitting device for splitting the primary laser beam into at least two secondary laser beams, wherein the splitting device contains polarization prisms including plane refractive surfaces arranged for forming the secondary laser beams as collimated laser beams, and each of the collimated laser beams has a different propagation angle with respect to an optical axis of a focusing optic;
    the focusing optic for focusing the secondary laser beams into at least two volume elements in the sample; and
    a detecting device for detecting light emitted from the volume elements and for evaluating the detected light in order to obtain the at least one property to be analyzed.

12. The device according to claim 11, wherein the splitting device further comprises a mirror array having at least two mirrors forming reflecting surfaces.

13. The device according to claim 12, further comprising a profile shaping device adapted for profile shaping of the primary laser beam.

14. The device according to claim 13, wherein the profile shaping device comprises a neutral density filter or a diffraction beam shaper.

15. The device according to claim 11, wherein the polarization prisms comprises at least one Wollaston prism.

16. The device according to claim 11, wherein a mirror array comprising at least two mirrors is arranged between the at least one of the polarization prisms prism and the focusing optic.

17. The device according to claim 12, wherein the mirrors of the mirror array are movable for adjusting the propagation angles of the secondary laser beams.

18. The method of claim 1, further comprising:
    parallel analyzing a plurality of samples;
    high-throughput screening a plurality of samples;
    obtaining time-resolved end or spatial-resolved fluorescence spectroscopic measurements;
    conducting fluorescence correlation spectroscopy;
    obtaining fluorescence coincidence measurements; and/or
    obtaining fluorescence fluctuation measurements.

19. A method for analyzing properties of a sample by measuring fluorescence parameters in multiple foci, said method comprising the steps of:
    splitting a collimated primary laser beam with polarization prisms of a splitting device into at least two collimated secondary laser beams and deflecting the secondary laser beams such that the secondary laser beams propagate at different propagation angles with respect to an optical axis of a focusing optic;

focusing the secondary laser beams with the focusing optic into at least two volume elements in the sample;

detecting light emitted from the volume elements with a detecting device; and processing with a signal processing unit a signal from the detecting device to record and/or display a representation of the properties.

* * * * *